United States Patent [19]

Kanojia et al.

[11] Patent Number: 4,556,739

[45] Date of Patent: Dec. 3, 1985

[54] 3,4-DIALKOXY-2-ALKYLCARBONYL ANALINO COMPOUNDS

[75] Inventors: Ramesh M. Kanojia, Somerville; Victor T. Bandurco, Bridgewater; Seymour D. Levine, North Brunswick, all of N.J.; Dennis M. Mulvey, New Hope; Alfonso J. Tobia, Doylestown, both of Pa.

[73] Assignee: Ortho Pharmaceutical Corporation, Raritan, N.J.

[21] Appl. No.: 627,139

[22] Filed: Jul. 2, 1984

Related U.S. Application Data

[63] Continuation-in-part of Ser. No. 537,232, Sep. 29, 1983.

[51] Int. Cl.⁴ .............................................. C07C 87/52
[52] U.S. Cl. .................................... 564/443; 544/286; 560/43; 562/433
[58] Field of Search ......................... 544/286; 564/443

[56] References Cited

U.S. PATENT DOCUMENTS

| | | | |
|---|---|---|---|
| 3,591,323 | 7/1971 | Kalopissis et al. | 564/443 |
| 3,983,120 | 9/1976 | Beverung et al. | 544/286 |
| 3,988,340 | 10/1976 | Partyka et al. | 544/286 |
| 4,146,717 | 3/1979 | Yamamoto et al. | 544/286 |
| 4,202,895 | 5/1980 | Inaba et al. | 544/286 |

*Primary Examiner*—Glennon H. Hollrah
*Assistant Examiner*—James H. Turnipseed
*Attorney, Agent, or Firm*—Benjamin F. Lambert

[57] ABSTRACT

A process for preparing 4-alkyl-2(1H)quinazolinone-1-alkanoic acid derivatives is described. The 4-alkyl-2(1H)quinazolinones are useful as cardiovascular agents.

2 Claims, No Drawings

3,4-DIALKOXY-2-ALKYLCARBONYL ANALINO COMPOUNDS

This is a continuation-in-part of application Ser. No. 537,232 filed Sept. 29, 1983.

The present invention relates to a method of preparing 4-alkyl-2(1H)quinazolinone-1-alkanoic acid derivatives.

In copending application Ser. No. 430,552 filed Sept. 30, 1982, now Pat. No. 4,490,374 a method is described for the preparation of dihydroxy-2(1H)quinazolinone-1-alkanoic acids. In the synthetic method described therein one of the key steps in the synthesis involves $N_1$-alkylation of a substituted quinazolinone by reaction with a Michael acceptor such as, for example, methyl acrylate in the presence of a suitable base to give the corresponding $N_1$-propionic acid methyl ester. Although generally applicable, the process is not well suited for the synthesis of the 8-substituted $N_1$-alkylated quinazolinones.

By the present invention, a method is described for the synthesis of substituted 4-alkyl-2(1H)quinazolinones having substitution in the 8-position. However, compounds having substituents in positions other than the 8-position can also be prepared by the novel process. Many of the compounds produced by the novel synthetic method are novel compounds and as such are included as part of this invention.

The substituted 4-alkyl-2(1H)quinazolinones which can be synthesized by the novel process have the following structural formula:

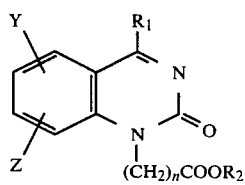

wherein n is an integer from 2–6; $R_1$ is lower alkyl having 1–4 carbon atoms; $R_2$ is hydrogen and lower alkyl having 1–4 carbon atoms; and Y and Z are hydroxy and lower alkoxy having 1–4 carbon atoms; also included are the pharmaceutically acceptable acid addition salts of the quinazolinones, such as, for example, the hydrochlorides, the hydrobromides and the hydroiodides.

Substituted 2(1H)quinazolines have been reported in the literature [Budesinsky et al., Coll. Czech. Chem. Commun., 37, 2779(1972). Belgian Pat. No. 765947 (11)]. However, none of the reported substituted quinazolinones are substituted with an alkanoic acid residue at the $N_1$ position or have a hydroxy group on the benzene ring. U.S. Pat. No. 3,926,993 describes the preparation of 1-alkyl-4-phenyl-2(1H)quinazolinones from 2-aminobenzophenones, however, no method is described in the patent for regioselectively alkylating the $N_1$-nitrogen.

The novel substituted 2(1H)quinazolinones of the present invention are renal vasodilators. As such they reduce vascular resistance to renal blood flow and are therefore useful as cardiovascular agents.

The substituted quinazolinones can be synthesized according to the following schematic diagram:

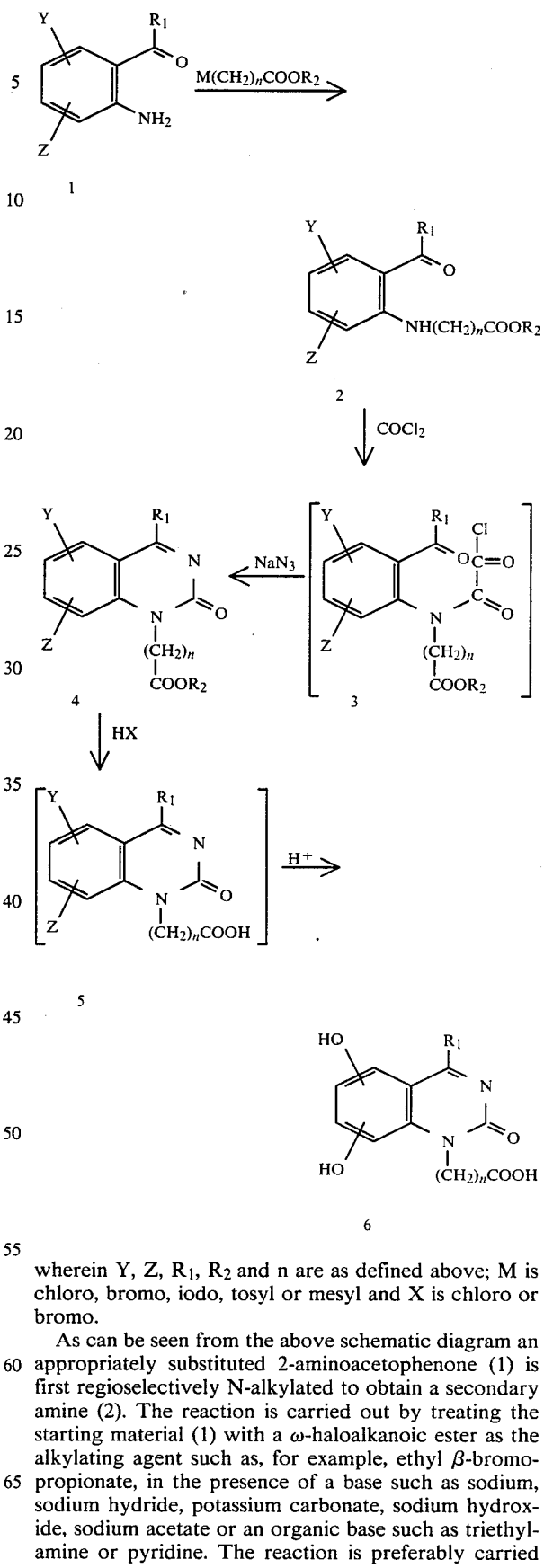

wherein Y, Z, $R_1$, $R_2$ and n are as defined above; M is chloro, bromo, iodo, tosyl or mesyl and X is chloro or bromo.

As can be seen from the above schematic diagram an appropriately substituted 2-aminoacetophenone (1) is first regioselectively N-alkylated to obtain a secondary amine (2). The reaction is carried out by treating the starting material (1) with a ω-haloalkanoic ester as the alkylating agent such as, for example, ethyl β-bromopropionate, in the presence of a base such as sodium, sodium hydride, potassium carbonate, sodium hydroxide, sodium acetate or an organic base such as triethylamine or pyridine. The reaction is preferably carried out neat with an excess of the haloalkanoic ester and the base at a temperature between 100°–155° C. Alternatively, the reaction may be carried out in a solvent mixture such as sodium acetate and acetic acid. Other solvents which may be employed include toluene, xylene, dimethylsulfoxide or dimethylformamide. In addition to ethyl β-bromopropionate, chloro, bromo, iodo, tosyl and mesyl lower alkyl esters of acetic, butyric, valeric, and caproic acid may be employed. The N-alkylation may also be carried out with the help of a phase transfer reagent or a crown ether and an acrylic acid derivative.

The secondary anilino compound (2) is then treated with an excess of an oxalyl halide, preferably oxalyl chloride, with or without an inert solvent. Where a solvent is employed, solvents such as benzene and methylene chloride can be employed. The reaction can be carried out at a temperature between 0°–50° C. The reaction is preferably carried out at room temperature. The oxamyl halide (3) obtained as the product is then added to a solution of sodium azide to form the quinazolinone (4). The reaction with sodium azide is preferably carried out at temperatures between −5° C. and room temperature. The preferred temperature range is −5° C.–0° C. Solvents which can be employed include acetone and aqueous acetone. In some cases, the quinazolinone (4) precipitates at this stage in the synthesis. Any precipitate which forms is collected and purified by techniques known to those skilled in the art.

In those cases where Y and/or Z are alkoxy, hydrolysis of the $N_1$-substituted quinazolinone (4) may be carried out either stepwise by first deesterifying the compound with aqueous acid to give the free acid (5) as its acid salt and then dealkylating the free acid (5) with a suitable dealkylating reagent. For example, when Y and/or Z is methoxy, demethylation may be effected by refluxing the quinazolinone (5) in HBr/acetic acid or aqueous hydrogen bromide. However, complete hydrolysis of the quinazolinone (4) can be achieved by refluxing it with HBr/acetic acid or hydrogen iodide to obtain the free acid as the acid salt. The acid salts can be converted to the free quinazolinone by neutralization techniques known to those skilled in the art.

The substituted acetophenones which are the starting materials in the preparation of the substituted 4-alkyl-2(1H)quinazolinones are prepared by methods known to those skilled in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility of for preservative purposes, may be included. Injectable suspensions may also be prepared, in which case appropriate liquid carriers, suspending agents and the like may be employed. The pharmaceutical compositions will generally contain, per dosage unit, e.g., tablet, capsule, powder, injection, teaspoonful and the like, from about 15 to about 300 mg/kg and preferably from about 30 to about 200 mg/kg of the active ingredient.

The following examples describe the invention in greater particularity and are intended to be a way of illustrating but not limiting the invention.

EXAMPLE 1

2'-(N-2-Carbethoxyethylamino)-3',4'-dimethoxyacetophenone

Triethylamine (19.4 g, 192 mM) was added to a mixture of 2'-amino-3',4'-dimethoxyacetophenone (25 g, 128 mM) and ethyl 3-bromopropionate (139 g, 770 mM), in a 250 mL flask (equipped with a large stirring bar, reflux condenser and nitrogen inlet). The pale solid which formed was stirred at 135° C. for 5 hours. The brown homogeneous oil which formed was then cooled to 10° C. and 200 mL of 2% $NaHCO_3$ was added. The solution was then extracted with $CHCl_3$ (3×100 mL), the organic layer washed with $H_2O$ (100 mL) and dried over $MgSO_4$. Following filtration, the $CHCl_3$ and most of the bromopropionate were removed under reduced pressure. The oily residue was charged onto a 10×75 cm, SilicAR CC-7 column (800 g, hexane packed) and eluted with 5 to 20% ethyl acetate/hexane, collecting 1 L fractions. Evaporation of fractions 7–9 gave purified 2'-(N-2-carbethoxyethylamino)-3',4'-dimethoxyacetophenone as a yellow oil (5.86 g, 15%); UV (EtOH) nm: 244 (ε29110), 284 (ε11480); MS (Probe) 295 (M+).

EXAMPLE 2

6'-Acetyl-N-β-carbethoxyethyl-2',3'-dimethoxyoxaniloyl chloride

2'-(N-2-Carbethoxyethylamino)-3',4'-dimethoxyacetophenone (5.8 g, 19.66 mM) was dissolved in $CH_2Cl_2$ (11 mL, dried over $MgSO_4$) and added slowly to cold (5° C.) oxalyl chloride (14.5 g, 114 mM). The solution was allowed to stir at room temperature for one hour after which time the solvent and excess $(COCl)_2$ were removed at reduced pressure, below 30° C. The red, oily residue of crude 6'-acetyl-N-β-carbethoxyethyl-2',3'-dimethoxyxaniloyl chloride was used in the next step without further purification.

EXAMPLE 3

7,8-Dimethoxy-4-methyl-2-(1H)quinazolinone-1-propionic acid ethyl ester

6-Acetyl-N-β-carbethoxyethyl-2',3'-dimethoxyxaniloyl chloride (42.25 mM) was dissolved in acetone and quickly added to an aqueous $NaN_3$ solution (2.75 g, 42.25 mM) which was stirred at 5° C. Following the addition, the solution was stirred at room temperature for 3 hours. About 70% of the solvent was removed by evaporation in vacuo, below 40° C. The residue was extracted with $CHCl_3$ (3×175 mL) and washed with brine (100 mL). The organic extracts were dried (MgSO$_4$), filtered and evaporated at reduced pressure. Trituration of the residue with ether/hexane gave 7,8-dimethoxy-4-methyl-2(1H)quinazolinone-1-propionic acid ethyl ester as a yellow solid (4.56 g, 73%), mp 128°–130° C.

EXAMPLE 4

7,8-Dihydroxy-4-methyl-2(1H)quinazolinone-1-propionic acid Hydrobromide 7,8-Dimethoxy-4-methyl-2(1H)quinazolinone-1-propionic acid ethyl ester (2 g, 6.25 mm) was dissolved in HBr (22 mL, 48%) and AcOH (20 mL, glacial) and refluxed for two days. Upon cooling a yellow crystalline solid separated which was isolated by filtration and washed with acetone to give purified 7,8-dihydroxy-4-methyl-2(1H)quinazolinone-1-propionic acid hydrobromide hemihydrate (1.27 g, 59%), mp 236°–238° C.

EXAMPLE 5

7,8-Didhydroxy-4-methyl-2(1H)quinazolinone-1-propionic acid

The free base was obtained by treating the HBr salt (1.32 g, 3.73 mm) with a solution of NaHCO$_3$ (0.392 g, 4.66 mm) in H$_2$O and dried to give purified 7,8-dihydroxy-4-methyl-2(1H)quinazolinone-1-propionic acid, ¾ hydrate, (0.84 g, 85%) mp 218°–220° C.

EXAMPLE 6

2'-(N-2-Carbethoxyethylamino)-3',5'-dimethoxyacetophenone

2'-Amino-3'-5'-dimethoxyacetophenone (57 g, 0.29 mol), sodium acetate (27.4 g, 0.33 mol) and ethyl 3-bromopropionate (277 ml, 2.2 mol) were added to acetic acid (356 mL) and stirred at reflux for 5 hours. The solution was poured into water and neutralized with NaOH (120 g in 1 L H$_2$O) and excess K$_2$CO$_3$. The solution was extracted with 2×2 and 6×1 L CH$_2$Cl$_2$. The extracts were combined, dried (MgSO$_4$) and added to a 3" column containing 2.3 kg silicic acid (SilicAR, CC-7) for chromatography. The first 6 L of eluent contained bromo ester and were discarded. After all the solution had been added elution was continued with 7.5% ethyl acetate in CH$_2$Cl$_2$ collecting 1 L fractions. Fractions 4 to 19 contained substituted aminoacetophenone (total wt 57.2 g, 66.3% yield) as a dark red liquid, IR (neat) µ: 3.03, 5.76, 6.08, 6.18; 295 (M+).

EXAMPLE 7

6'-Acetyl-N-β-carbethoxyethyl-2',4'-dimethoxyoxaniloyl chloride

2'-(N-β-Carbethoxyethylamino)-3',5'-dimethoxyacetophenone (5.30 g, 16.95 mM) in CH$_2$Cl$_2$ (35 mL) was slowly added (45 min.) to cold (5°–10° C.) oxalyl chloride (12.48 g) and the mixture stirred at room temperature for 1 hour. The solvent and excess (COCl$_2$) were removed in vacuo at 30° C. to give the title oxaniloyl chloride as a red oil (6.4 g) which was immediately used up in the next step, without further purification.

EXAMPLE 8

6,8-Dimethoxy-4-methyl-2(1H)quinazolinone-1-propionic acid ethyl ester

6'-Acetyl-N-β-carbethoxyethyl-2',4'-dimethoxyoxaniloyl chloride (6.4 g) in acetone (36 mL) was cooled to 15° C. and added to a stirred solution of NaN$_3$ (2.3 g, 35 mM) in H$_2$O (7.5 mL) at 10° C. The mixture was allowed to warm to room temperature and stirred for an additional 3.5 hours. Most of the solvent was removed in vacuo at 30° C. and the residue extracted with CHCl$_3$ (3×175 mL). The organic layer was washed with brine, dried (MgSO$_4$), filtered and the solvent evaporated in vacuo. The crude product was immediately chromatographed on a silica gel column (30×5 cm, SilicAR CC-7) using CHCl$_3$ and then 2% methanol/CHCl$_3$ as the eluent to isolate the product (3.6 g, 66%) as an oil [MS: 320 (M+)] and was immediately reacted with 1N HCl to convert it to the free acid as follows.

EXAMPLE 9

6,8-Dimethoxy-4-methyl-2(1H)quinazolinone-1-propionic acid Monohydrochloride Crude 6,8-dimethoxy-4-methyl-2(1H)quinazolinone-1-propionic acid ethyl ester (3.6 g, 11.25 mM) was dissolved in 1N HCl (44 mL) and stirred at room temperature for 2 days. The solvent was evaporated in vacuo (60°–70° C.) and the residue triturated with acetone to isolate 6,8-dimethoxy-4-methyl-2(1H)quinazolinone-1-propionic acid monohydrochloride as a yellow crystalline solid (2.70 g, 39%), mp 213° C.

EXAMPLE 10

6,8-Dimethoxy-4-methyl-2(1H)quinazolinone-1-propionic acid

The monohydrochloride salt when treated with water dissociates to give the free base as a solid, mp 243°–245° C. IR (KBr): 5.80, 6.19, 6.37; NMR (TFA): identical to that of the hydrochloride salt in TFA.

EXAMPLE 11

6,8-Dihydroxy-4-methyl-2-(1H)quinazolinone-1-propionic acid Monohydroiodide 6,8-Dimethoxy-4-methyl-2(1H)quinazolinone-1-propionic acid (1.75 g, 5.32 mM) was dissolved in hydriodic acid (48%, 30 mL) and refluxed for a total of 9 hours. The solution was evaporated at 75°–80° C. (hi-vac) to give a reddish semi-solid which was triturated with acetone:ethyl acetate (5:95; 15 mL) and then the solvent decanted. The solid was washed with ether (10×30 mL) carefully decanting each time and then filtered and washed with ether (3×30 mL) to give purified 6,8-dihydroxy-4-methyl-2(1H)quinazolinone-1-propionic acid monohydroiodide as an orange solid (860 mg, 40%): mp 240°–246° C.

EXAMPLE 12

6,8-Dihydroxy-4-methyl-2(1H)quinazolinone-1-propionic acid

The hydroiodide salt of the 6,8-dihydroxy-4-methyl-2(1H)quinazolinone-1-propionic acid (581 mg, 1.45 mM) was added to an aqueous NaHCO$_3$ solution (122 mg, 1.45 mM) at room temperature and stirred for 20 minutes. The pptd. free base was filtered and carefully washed with ice cold H$_2$O (3×2.5 mL) to give purified 6,8-dihydroxy-4-methyl-2(1H)-quinazolinone-1-propionic acid as a yellow solid (310 mg, 81%), mp 255°–257° C.

EXAMPLE 13

2'-(N-2-Carbethoxyethylamino)-3',6'-dimethoxyacetophenone

Triethylamine (19.4 g, 192 mM) was added to a mixture of 2'-amino-3',6'-dimethoxyacetophenone (2.5 g, 128 mM) and ethyl 3-bromopropionate (139 g, 770 mM) in a 250 mL flask. The pale solid complex so formed was stirred at 135° for 2 hours with a large and heavy stirring bar. During this time the complex became a homogeneous brown oil. This oil was cooled to 10° C. and 200 mL of 2% NaHCO$_3$ was added to the reaction mixture. The solution was then extracted with CHCl$_3$ (3×100 mL) and the organic layer washed with H$_2$O (100 mL) and then dried over MgSO$_4$. After filtration, the CHCl$_3$ and most of the bromopropionate were removed under reduced pressure. The oily residue was put on a 10×60 cm, SilicAR CC-7 column (500 g) and eluted with 5-20% ethyl acetate/hexane, collecting 1 L fractions. Evaporation of fractions 5 and 6 gave purified 2'-(N-2-carbethoxyethylamino)-3',6'-dimethoxyacetophenone (9.97 g, 26%); IR (neat) $\mu$: 3.3, 5.78, 5.8, 6.25.

EXAMPLE 14

2-Acetyl-$\beta$-carbethoxyethyl-3',6'-dimethoxyoxaniloyl chloride

2'-(N-2-Carbethoxyethyl-3',6'-dimethoxyacetophenone (6.0 g, 10.27 ml, 20.3 mM) was dissolved in CH$_2$Cl$_2$ (35 mL) and slowly added to cold (5° C.) oxalyl chloride (15 g, 118 mM). The solution was stirred at room temperature for one hour, after which the solvent and excess (COCl)$_2$ were removed under reduced pressure below 30° C. The red, oily residue of crude 2'-acetyl-N-$\beta$-carbethoxyethyl-3',6'-dimethoxyoxaniloyl chloride was used in the following step without further purification.

EXAMPLE 15

5,8-Dimethoxy-4-methyl-2(1H)quinazolinone-1-propionic acid ethyl ester

6'-Acetyl-$\beta$-carbethoxyethyl-2',6'-dimethoxyoxaniloyl chloride (7.84 g, 20.3 mM) was dissolved in acetone (30 mL), cooled (0°-5° C.) and quickly added to a cooled 15° C. and stirred aqueous NaN$_3$ solution (2.66 g/5 mL, 41 mM). Following the addition, the solution was stirred at room temperature for three hours. Approximately 70% of the solvent was removed by evaporation in vacuo, below 40° C., and the residue extracted with CHCl$_3$ (3×175 mL). The organic layer was washed with brine (100 mL), dried (MgSO$_4$), filtered and evaporated at reduced pressure. The crude product was chromatographed on a 4×30 cm, CHCl$_3$ packed, SilicAR CC-7 column (300 g) using 4% methanol/CHCl$_3$ as the eluent and collecting 500 mL fractions. Evaporation of fractions 6-9 gave purified 5,8-dimethoxy-4-methyl-2(1H)quinazolinone-1-propionic acid ethyl ester as a yellow solid (2.61 g, 38%), mp 96°-97° C.

EXAMPLE 16

5,8-Dihydroxy-4-methyl-2(1H)quinazolinone-1-propionic acid

Substituting 5,8-dimethoxy-4-methyl-2(1H)quinazolinone-1-propionic acid ethyl ester for 6,8-dimethoxy-4-methyl-2(1H)quinazolinone-1-propionic acid ethyl ester and treating it with HI as described for the preparation of 6,8-dihydroxy-4-methyl-2(1H)quinazolinone-1-propionic acid, one obtains 5,8-dihydroxy-4-methyl-2(1H)quinazolinone-1-propionic acid.

EXAMPLE 17

6'-(N-2-Carbethoxyethylamino)-2',3'-dimethoxyacetophenone

A. A slurry of 2',3'-dimethoxy-6'-nitrobenzoic acid (22.7 g, 0.1 mole) in ether (850 ml) was treated with a hexane solution of methyl lithium (445 ml of a 1.6M solution in n-hexane). The mixture was refluxed for two days and then cooled. Cold water (250 ml) was added slowly. Removal of the solvent from the organic layer gave a light brownish residue. Crystallization from isopropanol afforded 2',3'-dimethoxy-6'-nitroacetophenone (42% yield), mp 64°-66° C. Catalytic hydrogenation of 2,3-dimethoxy-6-nitroacetophenone in MeOH with 10% Pd/C in a Parr apparatus afforded 6'-amino-2',3'-dimethoxyacetophenone (95% yield), mp 57°-58° C.

B. Triethylamine (3.80 g, 5.35 mL, 38.46 mM) was at once added under N$_2$ to a stirred mixture of 6'-amino-2',3'-dimethoxyacetophenone (2.5 g, 12.8 mM) and ethyl 3-bromopropionate (13.93 g, 9.86 mL, 76.93 mM) at room temperature. Immediately the reaction mixture solidified. This was heated under N$_2$ to 135°-145° C. (bath temperature) for a period of 3 hours, while periodically stirring the solid reaction mixture to form a uniformly soft, semisolid mass. After cooling, the reaction was treated with 10% NaHCO$_3$ (50 mL) and extracted with CH$_2$Cl$_2$ (3×60 mL). The organic layer, after the H$_2$O wash, drying (Na$_2$SO$_4$), and the removal of the solvent in vacuo, gave a dark brown oily residue (5.3 g). This was chromatographed on a column of SilicAR CC-7 (350 g, 57 cm × 5 cm) packed in hexane and eluted with increasing proportions of ethyl acetate/hexane, collecting 1 L fractions. Fraction 6, eluting with 15% ethyl acetate/hexane gave, upon removal of the solvent in vacuo, purified 6'-(N-2-carbethoxyethylamino)-2',3'-dimethoxyacetophenone (0.452 g, 12%) as a light yellow oil. IR (neat) $\mu$: 2.97, 5.75, 6.10.

EXAMPLE 18

2'-Acetyl-N-$\beta$-carbethoxyethyl-3',4'-dimethoxyoxaniloyl chloride

By substituting 6'-(N-2-carbethoxyethylamino)-2',3'-dimethoxyacetophenone for 2'-(N-2-carbethoxyethylamino)-3',4'-dimethoxyacetophenone in the procedure described for the preparation of 6-acetyl-N-$\beta$-carbethoxyethyl 2',3'-dimethoxyoxaniloyl chloride one obtains 2'-acetyl-N-$\beta$-carbethoxyethyl-3',4'-dimethoxyoxaniloyl chloride.

EXAMPLE 19

5,6-Dimethoxy-4-methyl-2(1H)quinazolinone-1-propionic acid methyl ester

By substituting 2'-acetyl-N-$\beta$-carbethoxyethyl-3',4'-dimethoxyoxaniloyl chloride for 6-acetyl-N-$\beta$-carbethoxyethyl-3',4'-dimethoxyoxaniloyl chloride in the procedure described for the preparation of 7,8-dimethoxy-4-methyl-2(1H)quinazolinone-1-propionic acid ethyl ester one obtains 5,6-dimethoxy-4-methyl-2(1H)quinazolinone-1-propionic acid methyl ester, recrystallized from ethyl acetate, mp 118°-119° C. IR (KBr) $\mu$: 5.73, 6.08.

EXAMPLE 20

2'-(N-2-Carbethoxyethylamino)-4',5'-dimethoxyacetophenone

Triethylamine (3.88 g, 5.34 mL, 38.44 mM) was added at once under $N_2$ to a stirred mixture of 2'-amino-4',5'-dimethoxyacetophenone (2.5 g, 12.8 mM) and ethyl 3-bromopropionate (17.43 mL, 96.2 mM) at room temperature. Immediately the reaction mixture solified. This was heated under $N_2$ to 140°–150° C. (bath temp.) for a period of 4 hours during which the reaction mixture had partially liquified into a red-brown, viscous slurry. After cooling to room temperature it was treated with 5% $NaHCO_3$ solution (50 mL) and then extracted with $CH_2Cl_2$ (3×60 mL). The combined organic extracts were washed with $H_2O$, dried ($Na_2SO_4$) and evaporated in vacuo to remove $CH_2Cl_2$ (low vacuum) and excess 3-bromopropionate (under high vacuum at 50°–60° C.). The dark oily residue was chromatographed on a column of SilicAR CC-7 (300 g, 55.5×6 cm) packed in hexane. The sample was applied to the column in $CH_2Cl_2$ (50 mL) followed by elution with hexane and then with increasing proportions of ethyl acetate/hexane, collecting 1 L fractions. Fractions 10 and 11, afforded, upon evaporation to dryness 2'-(N-2-carbethoxyethylamino)-4',5'-dimethoxyacetophenone as a waxy crystalline solid (1.33 g, 35.2%), mp 73°–75° C.

EXAMPLE 21

6-Acetyl-N-β-carbethoxyethyl-3',4'-dimethoxyoxanilloyl chloride

By substituting 2'-(N-2-carbethoxyethylamino)-4',5'-dimethoxyacetophenone for 2'-(N-2-carbethoxyethylamino)-3',4'-dimethoxyacetophenone in the preparation of 6'-acetyl-N-β-carbethoxyethyl-2',3'-dimethoxyoxaniloyl chloride, one obtains 6'-acetyl-N-β-carbethoxyethyl-3',4'-dimethoxyoxaniloyl chloride.

EXAMPLE 22

6,7-Dimethoxy-4-methyl-2(1H)quinazolinone-1-propionic acid ethyl ester

By substituting 6'-acetyl-N-β-carbethoxyethyl-3',4'-dimethoxyoxaniloyl chloride for 6'-acetyl-N-β-carbethoxyethyl-2',3'-dimethoxyoxaniloyl chloride in the procedure described for the preparation of 7,8-dimethoxy-4-methyl-2(1H)quinazolinone-1-propionic acid ethyl ester, one obtains 6,7-dimethoxy-4-methyl-2(1H)quinazolinone-1-propionic acid ethyl ester; 1R (KBr) $\mu$: 5.80, 6.06; MS (probe): 320 (M+).

EXAMPLE 23

2'-(N-3-Carbethoxypropylamino)-4',5'-dimethoxyacetophenone

Ethyl-4-bromobutyrate (190.7 g, 978 mM) was added with stirring to 2'-amino-4',5'-dimethoxyacetophenone (31.8 g, 163 mM) in triethylamine (33.9 mM) and the reaction mixture was heated at 110° C. for one hour. After cooling to room temperature 100 mL of 2% $NaHCO_3$ was added and the reaction mixture was stirred for sixteen hours. A yellow solid formed which was dissolved in $CHCl_3$ (250 mL). The aqueous phase was extracted with $CHCl_3$ (4×200 mL), the organic extracts were combined and dried over $MgSO_4$, filtered, and the solvent removed in vacuo to give a semisolid residue. The residue was chromatographed on SilicAR CC-7 and the appropriate fractions were crystallized upon standing from ether to afford the title compound in 62% yield, ,mp 74°–76° C.

EXAMPLE 24

2'-(N-4-Carbethoxybutylamino)-4',5'-dimethoxyacetophenone

When ethyl-5-bromopentanoate is employed instead of ethyl-4-bromobutyrate in Example 23 the title compound is obtained.

EXAMPLE 25

6,7-Dimethoxy-4-methyl-2(1H)quinazolinone-1-butanoic acid ethyl ester

Oxalyl chloride (110.4 g, 87 mM) was added in a slow stream with stirring to a solution of 2'-(N-3-carboxypropylamino)-4',5'-dimethoxyacetophenone (27.0 g, 87 mM) in $CH_2Cl_2$ (350 mL). The reaction mixture was stirred for thirty minutes at room temperature. The solvent was removed in vacuo and the residue treated with acetone (150 mL). The reaction mixture was stirred while a solution of sodium azide (16.96 g, 26 mM) in $H_2O$ (60 mL) was added slowly with stirring for sixteen hours. The solvent was removed in vacuo to give a residue which was chromatographed on a SilicAR CC-7 column to afford the title compound in 19% yield, mp 137°–139° C.

EXAMPLE 26

6,7-Dimethoxy-4-methyl-2(1H)quinazolinone-1-pentanoic acid ethyl ester

When 2'-(N-4-carbethoxybutylamino)-4',5'-dimethoxyacetophenone is treated with oxalyl chloride and then sodium azide as in Example 25, the title compound is obtained.

EXAMPLE 27

6,7-Dihydroxy-4-methyl-2(1H)quinazolinone-1-butanoic acid ¼ Hydrate

When 6,7-dimethoxy-4-methyl-2(1H)quinazolinone-1-butanoic acid ethyl ester is refluxed with excess 40% aqueous HBr for 24 hours the title compound is afforded in 80% yield, mp 288°–299° C.

EXAMPLE 28

6,7-Dihydroxy-4-methyl-2(1H)quinazolinone-1-pentanoic acid

When 6,7-dimethoxy-4-methyl-2(1H)quinazolinone-1-pentanoic acid ethyl ester is hydrolyzed with 40% aqueous HBr for 24 hours as in Example 27 the title compound is obtained.

The renal vasodilator activity of the substituted quinazolinones is determined by the following general procedure:

METHODS

Adult mongrel dogs are anesthetized and surgically prepared for electromagnetic measurement of renal artery blood flow. A carotid artery is cannulated for measuring arterial blood pressure and drugs are administered intraveneously. Heart rate (HR) is monitored by a cardiotachometer. Renal vascular resistance (RVR) is calculated as the ratio of mean arterial blood pressure (MABP)/renal artery blood flow (RBR). Cumulative dose-response data are obtained by infusing the test drug at progressively increasing (usually three-fold)

infusion rates, each dose being infused for five minutes. The maximum percent change from pre-drug control is quantitated for each parameter. Reductions in renal vascular resistance represent renal vasodilation. The activity of some representative compounds of this invention is listed below.

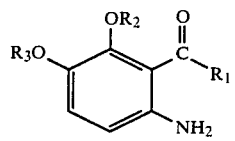

| STRUCTURE | TOTAL CUMULATIVE DOSE mg/kg, i.v. | PERCENT CHANGE FROM PRE-DRUG BASELINE | | | |
|---|---|---|---|---|---|
| | | RBF | RVR | MABP | HR |
| CH₃O-[ring]-CH₃ with N=C(CH₃), N-CH₂CH₂CO₂H, C=O, O-CH₃ | 15 | +49 | −29 | +6 | −20 |
| CH₃O-[ring]-OCH₃ with N=C(CH₃), N-CH₂CH₂CO₂H, C=O | 30 | +20 | −27 | −15 | 0 |
| HO-[ring]-OH with N=C(CH₃), N-CH₂CH₂CO₂H, C=O | 15 | +22 | −19 | 0 | −3 |
| HO-[ring]-OH with N=C(CH₃), N-CH₂CH₂CO₂H, C=O | 13.9 | +27 | −26 | −6 | −15 |

RENAL VASODILATOR ACTIVITY IN THE ANESTHETIZED DOG

We claim:
1. A compound of the formula wherein $R_1$, $R_2$ and $R_3$ are the same or different lower alkyl.

2. The compound of claim 1 wherein $R_1$, $R_2$ and $R_3$ are methyl.

* * * * *